United States Patent [19]
Hofmann

[11] Patent Number: 6,096,020
[45] Date of Patent: Aug. 1, 2000

[54] ELECTROPORATION EMPLOYING USER-CONFIGURED PULSING SCHEME

[75] Inventor: Günter A. Hofmann, San Diego, Calif.

[73] Assignee: Genetronics, Inc., San Diego, Calif.

[21] Appl. No.: 09/126,941

[22] Filed: Jul. 30, 1998

Related U.S. Application Data

[62] Division of application No. 08/709,615, Sep. 9, 1996, Pat. No. 5,869,326.

[51] Int. Cl.$^7$ .................................................. A61M 31/00
[52] U.S. Cl. ........................... 604/501; 604/20; 435/173.6
[58] Field of Search ............................... 604/20.21, 501; 435/173.6

[56] References Cited

U.S. PATENT DOCUMENTS

| | | | |
|---|---|---|---|
| 4,946,793 | 8/1990 | Marshall, III | 435/291 |
| 5,098,843 | 3/1992 | Calvin | 435/287 |
| 5,169,384 | 12/1992 | Bosniak et al. | 604/20 |
| 5,186,800 | 2/1993 | Dower | 435/172.3 |
| 5,273,525 | 12/1993 | Hofmann | 604/21 |
| 5,304,120 | 4/1994 | Crandell et al. | 604/21 |
| 5,389,069 | 2/1995 | Weaver | 604/21 |
| 5,422,272 | 6/1995 | Papp et al. | 435/173.4 |
| 5,501,662 | 3/1996 | Hofmann | 604/21 |
| 5,507,724 | 4/1996 | Hofmann et al. | 604/21 |

Primary Examiner—Corrine McDermott

[57] ABSTRACT

An electroporation method and apparatus generating and applying an electric field according to a user-specified pulsing scheme. Advantageously, one such pulse includes a low voltage pulse of a first duration, immediately followed by a high voltage of a second duration, immediately followed by a low voltage of a third duration. The low voltage electroporation field accumulates molecules at the surface of a cell, the appropriately high voltage field creates an opening in the cell, and the final low voltage field moves the molecule into the cell. The molecules may be DNA, portions of DNA, chemical agents, the receiving cells may be eggs, platelets, human cells, red blood cells, mammalian cells, plant protoplasts, plant pollen, liposomes, bacteria, fungi, yeast, sperm, or other suitable cells. The molecules are placed in close proximity to the cells, either in the interstitial space in tissue surrounding the cells or in a fluid medium containing the cells.

18 Claims, 4 Drawing Sheets

ELECTROPORATION EMPLOYING USER-CONFIGURED PULSING SCHEME

This application is a divisional of application Ser. No. 08/709,615 filed Sep. 9, 1996 now U.S. Pat. No. 5,869,326.

BACKGROUND OF THE INVENTION

1. Field of Invention

The present invention generally relates to electro-cell manipulation. More particularly, the invention concerns an electroporation apparatus and method for generating and applying an electric field according to a user-selected pulsing scheme to more efficiently introduce molecules into cells and minimize damage to cellular tissue.

2. Description of Related Art

A cell has a natural resistance to the passage of molecules through its membranes into the cell cytoplasm. Scientists in the 1970s first discovered "electroporation", where electrical fields are used to create pores in cells without causing permanent damage to them. Electroporation was further developed to aid in the insertion of various molecules into cell cytoplasm by temporarily creating pores in the cells through which the molecules pass into the cell.

Electroporation has been used to implant materials into many different types of cells. Such cells, for example, include eggs, platelets, human cells, red blood cells, mammalian cells, plant protoplasts, plant pollen, liposomes, bacteria, fungi, yeast, and sperm. Furthermore, electroporation has bene used to implant a variety of different materials, referred to herein as "implant materials", "implant molecules", "implant agents". Namely, these materials have included DNA, genes, and various chemical agents.

Electroporation has been used in both in vitro and in vivo procedures to introduce foreign material into living cells. With in vitro applications, a sample of live cells is first mixed with the implant agent and placed between electrodes such as parallel plates. Then, the electrodes apply an electrical field to the cell/implant mixture. Examples of systems that perform in vitro electroporation include the Electro Cell Manipulator ECM 600 product, and the Electro Square Porator T820, both made by the BTX Division of Genetronics, Inc.

With in vivo applications of electroporation, electrodes are provided in a caliper that grips the epidermis overlying a region of cells to be treated. Alternatively, needle-shaped electrodes may be inserted into the patient, to access more deeply located cells. In either case, after the implant agent is injected into the treatment region, the electrodes apply an electrical field to the region. Examples of systems that perform in vivo electroporation include the Electro Cell Manipulator ECM 600 product, and the Electro Square Porator T820, both made by the BTX Division of Genetronics, Inc.

One type of in vivo electroporation application under research is electrochemotherapy, which uses electroporation to deliver chemotherapeutic agents directly into tumor cells. This treatment is carried out by infusing an anticancer drug directly into the tumor and applying an electric field to the tumor between a pair of electrodes. The molecules of the drug are suspended in the interstitial fluid between and in and around the tumor cells. By electroporating the tumor cells, molecules of the drug adjacent many of the cells are forced or drawn into the cell, subsequently killing the cancerous tumor cell.

Electroporation in this application is especially beneficial because electroporation can help minimize the amount of implant agent used, these chemicals frequently being harmful to normal cells. In particular, less of the implant agent can be introduced into the tumorous area because the electroporation will enable more of the implant agent to actually enter the cell. Electroporation is also beneficial for chemotherapy because some of the most promising anti-cancer drugs, such as Bleomycin, normally cannot penetrate the membranes of certain cancer cells. However, recent experiments with electroporation demonstrated that it is possible to insert the Bleomycin directly into the cells.

Known electroporation techniques (both in vitro and in vivo) function by applying a brief high voltage pulse to electrodes positioned around the treatment region. The electric field generated between the electrodes causes the cell membranes to temporarily become porous, whereupon molecules of the implant agent enter the cells. In known electroporation applications, this electric field comprises a single square wave pulse on the order of 1000 V/cm, of about 100 $\mu$s duration. Such a pulse may be generated, for example, in known applications of the Electro Square Porator T820, made by the BTX Division of Genetronics, Inc.

Although known methods of electroporation may be suitable for certain applications, the electric field may actually damage the electroporated cells in some cases. For example, an excessive electric field may damage the cells by creating permanent pores in the cell walls. In extreme cases, the electric field may completely destroy the cell.

Attempting to ameliorate these undesirable effects, at least one application has proposed the use of multiple pulses. One application, for example, proposed use of an electromechanical relay to provide consecutive first and second pulses. S. I. Sukharev et al., Biophys. J. Vol. 63, November 1992, pp. 1320–1327. More particularly, Sukharev uses an electric field pulse 100 as shown in FIG. 1. The pulse 100 includes (1) a first, narrow duration, high voltage pulse 102, (2) a delay 103 of $\Delta t$, during which no pulse is generated, then (3) a second, wide duration, low voltage pulse 104. The first pulse 102 was intended to porate the membrane, whereas the second pulse 104 was intended to electrophorese DNA into the cell cytosol. Sukharev recognized that the delay 103 should not be excessive.

Although the Sukharev system may provide satisfactory results in some applications, this system may not be completely adequate for certain other applications. Some users may find, for example, that Sukharev's electroporation does not effectively move enough molecules of the implant agent into the target cells. This results from an excessive delay 103 between Sukharev's first 102 and second 104 pulses, as recognized by the present inventor. The pores of a cell, created by electroporation, stay open for a finite time, largely depending upon the cell's temperature. Thus, the effect of the first pulse may start to significantly decay (thereby closing the cell's pores) during the delay between the first and second pulses. In some applications, this may be sufficient to completely nullify the first pulse's effect upon the cell by the time the second pulse occurs. As a result, the efficacy of Sukharev's electroporation may be insufficient in some cases. Moreover, lacking an effective first pulse, the second pulse of Sukharev's system may need to be increased to the point where it permanently destroys cells.

The delay described above is inherent to the Sukharev system due to the use of electromechanical relays. Sukharev uses independent pulse generators, whose outputs are selectively coupled to output electrodes by a relay. As known in the art, however, the switching of an electromechanical relay typically takes a significant amount of time, sometimes even 50–100 ms. Therefore, the efficacy of the implant agent achieved by Sukharev may be too low for some applications.

Thus, as recognized by the present inventor, existing electroporation systems may not be suitable for certain applications due to the generation of an excessive electric field, or due to the delay between adjacent pulses. Furthermore, many existing electroporation systems lack sufficient control over the parameters of the electric field pulses such as amplitude, duration, number of pulses, etc.

SUMMARY OF THE INVENTION

Broadly, the present invention concerns an electroporation method and apparatus for generating and applying an electric field according to a user-specified pulsing scheme. One example of such a pulsing scheme includes a low voltage pulse of a first duration, immediately followed by a high voltage of a second duration, immediately followed by a low voltage of a third duration. The invention provides the low voltage electroporation field to accumulate molecules at the surface of a cell, the appropriately high voltage field to create an opening in the cell, and the final low voltage field to move the molecule into the cell.

The molecules may be genes or drugs such as DNA, portions of DNA, chemical agents or any other molecule. The molecules are placed in close proximity to the cells, either in the interstitial tissue surrounding the cells or in a fluid medium containing the cells.

Accordingly, one aspect of the present invention concerns a method of generating and applying an electric field according to a user-selected pulsing scheme to more efficiently introduce molecules into cells and minimize damage to cellular tissue.

A different aspect of the invention concerns an apparatus comprising an electrical pulse generator to generate and apply such a pulsing theme. One embodiment of such an apparatus utilizes the following components. First and second power supplies provide first and second respective output voltages. A transformer, with primary and secondary windings, has a pair of output terminals coupled to the secondary winding. A first switch, responsive to a first gating signal, applies the first output voltage to the primary winding. A second switch, responsive to a second gating signal, applies the second voltage directly to the output terminals. A controller receives user specification of an output pulse pattern, and provides the first and second gating signals to generate the specified output pulse pattern at the output terminals.

The present invention provides a number of distinct benefits. Generally, the invention is useful to introduce molecules of an implant agent into cells with significantly increased effectiveness. The treatment agent, for example, may include drugs for treating cancer, karposi's sarcoma, and a number of other diseases and conditions.

In contrast to prior arrangements using a constant level electric field, the stepped pulse of the invention minimizes cell damage by using a low voltage electric field before and after cell pores are created. The invention thus minimizes the exposure of cells to high voltage electric fields, reducing possible damage to the cells. Moreover, the stepped pulse of the invention also saves energy, since the first and third pulses use less voltage than prior arrangements.

In addition, by using electroporation to open cells for receipt of molecules of an implant agent, the invention increases the efficacy of the agent. Consequently, less of the implant agent is needed, thereby reducing any side-effects of the implant agent.

Another benefit of the invention is that, regardless of how long voltage is applied to the transformer's primary winding, resultant transformer saturation limits the duration of the corresponding output signal on the transformer's secondary winding. This prevents damage to the treated cells, which might otherwise result from prolonged application of voltage to the transformer's primary winding. Another advantage of the invention is that the transformer's output is floating, and therefore no substantial current will flow if the patient is connected to another earth or ground material.

The invention also provides a number of other benefits, as discussed in greater detail below.

BRIEF DESCRIPTION OF THE DRAWINGS

The nature, objects, and advantages of the invention will become more apparent to those skilled in the art after considering the following detailed description in connection with the accompanying drawings, in which like reference numerals designated like parts throughout, wherein.

DETAILED DESCRIPTION OF THE PREFERRED EMBODIMENTS

HARDWARE COMPONENTS & INTERCONNECTIONS

Figure 2:
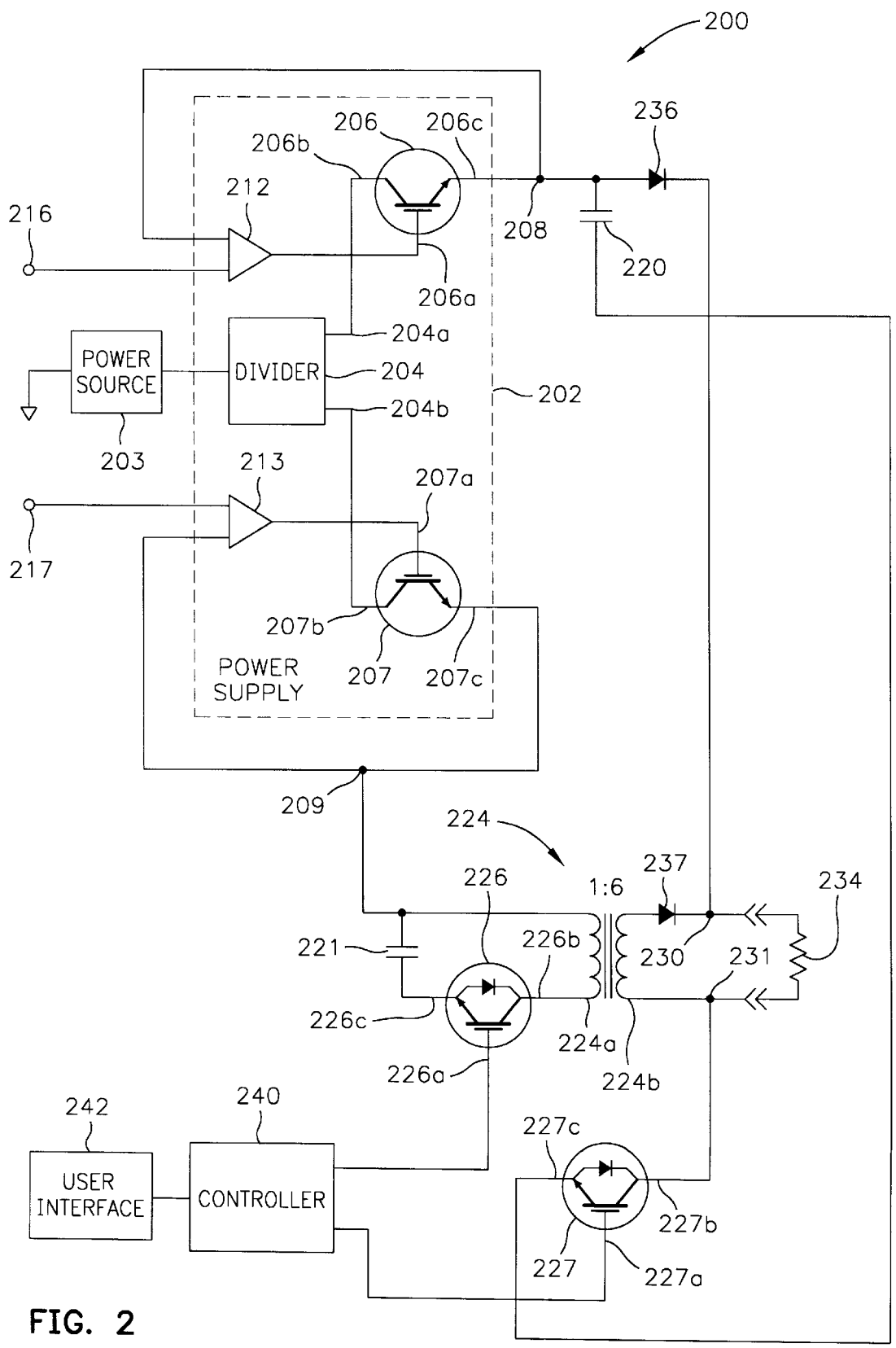
FIG. 2 is a diagram of the hardware components and interconnections of a pulse generator pursuant to one aspect of the present invention.
Figure 6:
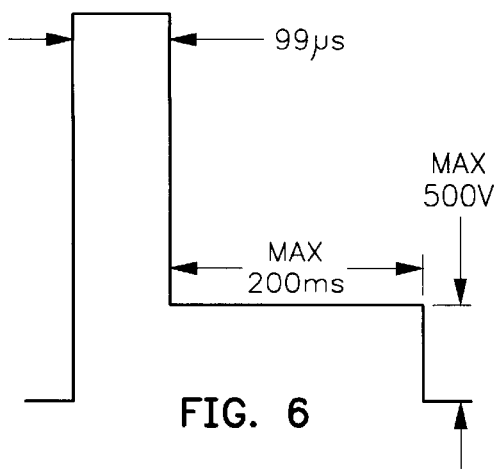

As mentioned above, one aspect of the present invention concerns an improved electrical pulse generator capable of generating and applying an electric field according to a user-selected pulsing scheme to more efficiently introduce molecules into cells and minimize damage to cellular tissue. FIG. 2 depicts an exemplary pulse generator 200. The generator 200 includes a number of different components, described as follows.

Power Supply

A power supply 202 provides a reliable source of desired voltage levels for use by the generator 200. The power supply 202 receives an input voltage, such as 110V or 220 VAC, from a power source 203. A divider 204 converts the input voltage into multiple reference voltages. In the illustrated embodiment, reference voltages of 500 V (D.C.) reside on the divider output lines 204a–204b.

These voltages are provided to collectors 206b–207b of first and second respective transistors 206–207. The transistors 206–207 are selectively gated to apply their input voltages to step voltage nodes 208–209. The selective gating of the transistors 206–207 is performed by respective comparators 212–213, which trigger gates 206a–207a of the transistors 206–207 when voltages at the step voltage nodes 208–209 dips below voltages established on step voltage input lines 216–217. For example, when the comparator 212 determines that the voltage on the step voltage node 208 is less than the voltage on the pre-set input line 216, the comparator 212 activates the gate 206a of the transistor 206, causing the transistor 206 to couple the input voltage of the divider 204 directly to the step voltage node 208. Thus, the transistors 206 maintain substantially constant voltages at the respective step voltage nodes 208–209 in accordance with the step voltage input lines 216–217.

Energy Reservoirs

The generator 200 also includes energy reservoirs 220–221 coupled to respective step voltage nodes 208–209. Exemplary energy reservoirs 220–221 may comprise capacitors, such as 3000 $\mu$F, 500 V electrolytic capacitors. These capacitors are appropriate for maximum step voltages 208–209 of 500 V (D.C.).

Transformer

The generator 200 also includes a transformer 224, which includes a primary winding 224a and a secondary winding 224b. The transformer 224 preferably demonstrates low leakage inductance to advantageously provide a fast pulse rise time, on the order of several microseconds. Preferably, the transformer 224 exhibits low inductance, on the order of several $\mu$H. These features may be provided by winding the transformer 224 with a single cable of twelve separate, twisted conductors of which six are connected in parallel for the primary, six are connected in series for the secondary. This provides a 1:6 step-up ratio. In addition, a separate low voltage D.C. bias winding around the core may be used to employ the full flux swing of the transformer's core. As an example, the transformer may utilize a core made of laminated iron.

The transformer 224 may advantageously be constructed to saturate if the pulse length exceeds a maximum prescribed value, thereby protecting a patient from excessive electrical energy. Preferably, the transformer 224 is capable of carrying 0.3 V-sec (3000 V×100 $\mu$sec) before saturation. Another advantage of the transformer 224 is that its output is floating, and no substantial current will flow if the patient is connected to another earth or ground potential.

The secondary winding 224b is coupled to output nodes 230–231, which are embodied by electrodes in the illustrated application. The electrodes (not shown) may comprise parallel plate electrodes, needle electrodes, caliper electrodes, or another arrangement of electrodes. Further discussion of caliper electrodes appears in (1) U.S. patent application Ser. No. 08/537,265, entitled "Method of Treatment Using Electroporation Mediated Delivery of Drugs and Genes", filed on Sep. 29, 1995, and (2) Dec. et al., "Electrochemotherapy—a novel method of cancer treatment", Cancer Treatment Reviews (1994) 20, 105–115. A useful example of needle electrodes is discussed in U.S. patent application Ser. No. 08/467,566, entitled "Needle Electrodes for Electroporation Mediated Delivery Of Drugs and Genes" filed on Jun. 6, 1995. Each of the aforementioned documents is hereby incorporated by reference in its entirety.

The load between the electrodes 230–231 is represented by a resistor 234. In the illustrated embodiment, the load 234 comprises a number of cells, which may be in vitro or in vivo samples of eggs, platelets, human cells, red blood cells, mammalian cells, plant protoplasts, plant pollen, liposomes, bacteria, fungi, yeast, sperm, or other cells.

To protect the energy reservoir 220 and power supply 202, a diode 236 may be placed between the energy reservoir 220 and the electrode 230. Likewise, to protect the energy reservoir 221 and power supply 220, a diode 237 may be placed between the secondary winding 224b and the electrode 230.

Switches

The generator 200 also includes switches 226–227 to selectively enable current to flow through the primary and secondary windings 224a–224b, respectively. In one exemplary construction, each switch 226–227 may comprise an insulated gate bipolar transistor ("IGBT"), such as Fuji Electric brand IMBI400F-060 model IGBT.

The switch 226 and the energy reservoir 221 are coupled in series, this series combination being attached in parallel with the primary winding 224a. When voltage is applied to a gate 226a of the switch 226, the collectors 226b and emitter 226c are electrically connected. Thus, the energy reservoir 221 is effectively placed in parallel with the primary winding 224a. This permits current from the energy reservoir 121 to flow through the primary winding 224a.

Similarly, the switch 227 and energy reservoir 220 are coupled in series, this series combination being attached in parallel with the secondary winding 224b. When voltage is applied to a gate 227a of the switch 227, the collectors 227b and emitter 227c are electrically connected. Thus, the energy reservoir 220 is effectively placed in parallel with the secondary winding 224b. This permits current from the energy reservoir 220 to flow through the load 234.

Advantageously, none of the energy reservoirs 220–221 or switches 226–227 grounds the windings 224a–224b. The windings 224a–224b are therefore electrically floating. As a result, no substantial current will flow through a patient or other load 234 that is connected to another earth or ground potential.

Controller

Another component of the generator 200 is the controller 240, which manages operation of the switches 226–227. Broadly, the controller 240 regulates the on-times and off-times of the switches 226–227 in accordance a specified schedule, thereby generating a predetermined pulsing scheme at the electrodes 230–231. When the controller 240 triggers the switch 227, the voltage of the energy reservoir 220 is applied to the electrodes 230–231. When the controller 240 triggers the switch 226, the voltage of the energy reservoir 220 is applied to the transformer 224, where it is multiplied by six and applied to the electrodes 230–231. The controller 220 may also trigger both switches 226–227 to apply an additive voltage, comprising the sum of the step voltages 208–209, to the electrodes 230–231.

The controller 240 may comprise a computer, digital or analog processing apparatus, programmable logic array, hard-wired logic circuit, application specified integrated circuit ("ASIC"), or another suitable device. In an exemplary embodiment, the controller 240 may comprise a PIL 16C64 Microchip microprocessor accompanied by appropriate RAM and ROM modules, as desired.

Preferably, the controller 240 is coupled to a user interface 242 for exchanging data with a user. In the illustrated example, the user may operate the user interface 242 to input a desired pulsing pattern to be applied to the electrodes 230–231.

As an example, the user interface 242 may include an alphanumeric keypad, touch screen, computer mouse, push-buttons and/or toggle switches, or another suitable component to receive input from a human user. The user interface 242 may also include a CRT screen, LED screen, LCD screen, liquid crystal display, printer, display panel, audio speaker, or another suitable component to convey data to a human user.

Preferable Design Parameters

The electrical requirements can be derived from the field strength, which was determined efficacious from in vitro experiments with tumor cells and drugs, typically 1200–1300 V/cm, and a pulse length of about 100 μsec. The maximum voltage of the generator derives from the maximum tumor size one wants to treat. In order to treat tumors up to 2 cm diameter with caliper electrodes (parallel plates) at field strength of 1300 V/cm, an operating voltage of 1300×2=2600 V is required; the generator was designed to generate 3000 V maximum to provide some extra margin.

The tissue/tumor specific resistivity was assumed to be as low as 100 Ohm×cm. With an electrode area of 3 cm×3 cm=9 cm$^2$, the resistance is 22 Ohm. the internal impedance of the generator should be at least a factor 10 lower than 22 Ohm so that no substantial drop in voltage occurs between charging and delivered voltage. With the maximum voltage of 3000 V and a load impedance of 22 Ohm, the switching requirements from a partial capacitor discharge to generate a square pulse are a very substantial 400 kW.

The desired maximum permeation pulse length is 100 μsec; this results in an energy per pulse of 40 J. For the collection and electrophoresis pulse parameters, a maximum voltage of 500 V and maximum pulse length of 200 msec may be used.

The maximum load current is about 136 A, which translates into a primary current of 6·136=816 A, which the switch has to carry and turn on and off. The switches 226–227 can preferably maintain continuous current 800 A for 1 msec. The maximum voltage is 600 V. Transient spikes are limited to a maximum of 550 V for a 10% safety margin. This required careful low inductance mechanical assembly to reduce transients and to be able to get as close as safely feasible to the maximum voltage limit of the IGBT.

The load impedance of 22 Ohm is transformed to the primary: 22/6×6–0.61 Ohm. A total internal impedance of 0.055 Ohm was achieved on the primary side of the transformer, which translates to an equivalent impedance of 1.98 Ohm on the secondary. Such a low impedance can lead to excessive currents in case of an arc or short circuit and these would destroy the expensive switching IGBT. The IGBT can be configured to contain a current limiting feature, which turns the switch off within a few μsec in case of excessive load currents such as might occur in case of an arc or a short circuit. By inducing an arc in the secondary, we measured a benign shut down of the IGBT within 5 μsec, as soon as the current exceeds about 900 A in the primary, corresponding to 150 A in the secondary.

The necessary capacitor size can be estimated from the maximum allowable voltage drop across the load 5%. The charge conducted in the primary pulse is 100 μs×816 A–0.08 Cb. If this should be 5% of the capacitor bank, the bank needs to hold 20×0.08=1.6 Cb. At 500 V maximum, the required capacity is C=Q/V=1.6/500=0.0032 F or 3200 μF. The energy stored in these capacitors is 400 Joule.

For the collection and electrophoresis pulse, a second capacitor discharge circuit delivers the longer pulse lengths (several 100 msec) and low voltage (500 V) without the pulse transformer. The low voltage circuit and the high voltage circuit are decoupled from each other by stacks of diodes 237 and 236.

OPERATION

In addition to the various hardware embodiments described above, a different aspect of the invention broadly concerns a method for generating a user-specified electric field pulsing pattern to achieve improved electroporation.

Data Storage Media

This method may be implemented, for example, by operating the controller 240 to execute a sequence of machine-readable instructions. These instructions may reside in various types of data storage media. In this respect, one aspect of the present invention concerns an article of manufacture, comprising a data storage medium tangibly embodying a program of machine-readable instructions executable by a digital data processor to perform method steps to generate a user-specified electric field pulsing pattern to achieve improved electroporation.

Figure 1:
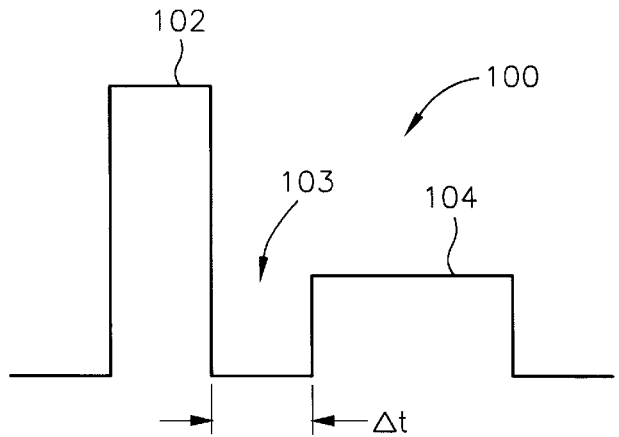
FIG. 1 is a diagram illustrating an electroporation waveform in accordance with the prior art.
Figure 3:
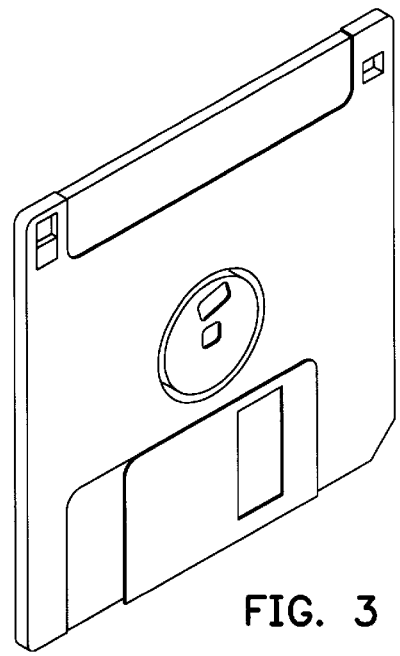
FIG. 3 is a diagram of an exemplary article of manufacture, comprising a data storage medium, in accordance with one aspect of the present invention.

This data storage medium may comprise, for example, RAM contained within the controller 240. Alternatively, the instructions may be contained in another data storage medium, such as a magnetic data storage diskette 300 (FIG. 3). Whether contained in the controller 240 or elsewhere, the instructions may instead be stored on another type of data storage medium such as DASD storage (e.g. a conventional "hard drive" or a RAID array), magnetic tape, electronic read-only memory (e.g. ROM), optical storage device (e.g. WORM), paper "punch" cards, or other data storage media. In an illustrative embodiment of the invention, the machine-readable instructions may comprise lines of compiled PIL 16C64 Microchip machine code.

Operational Steps

Figure 4:
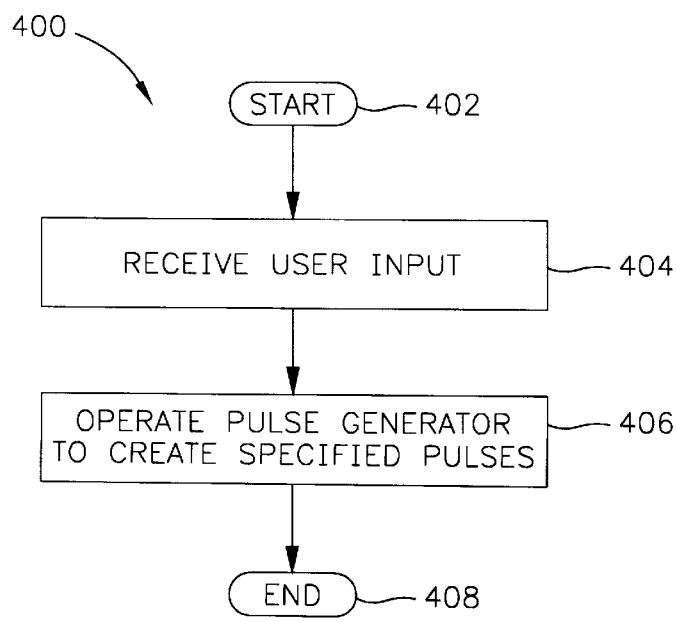
FIG. 4 is a flowchart illustrating an exemplary sequence of method steps in accordance with one aspect of the present invention.
Figure 5:
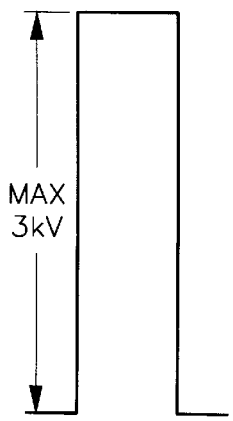
FIGS. 5–9 are drawings of illustrative electroporation pulsing schemes, pursuant to the invention.

As mentioned above, one aspect of the invention broadly concerns a method for generating a user-specified electric field pulsing pattern to achieve improved electroporation. FIG. 4 shows a sequence of methods steps 400 to illustrate one example of this aspect of the present invention. For ease of explanation, but without any limitation intended thereby, the sequence of FIG. 4 is described in the specific context of the pulse generator 200 described above.

After the steps 400 are initiated in task 402, the controller 240 in task 404 receives user input specifying an output pulse pattern of one or more output pulses. As an example, this user input may be received from the user interface 242. As an alternative, the user input may be received from another electronic device, or even a pre-stored record.

Preferably, the user input specified a duration for each pulse and also specifying either a "high" output voltage or a "low" output voltage. Next, for each pulse of low predetermined voltage, the pulse generator in task 404 generates the "low" predetermined voltage at the output terminals 230 and 231 for the specified duration. More particularly, the controller 240 may generate a low voltage pulse by gating the switch 227, thereby permitting the energy reservoir 220 to discharge through the load 234.

Also in task 404, high voltage pulses are generated at the secondary winding terminals by concurrently applying another voltage to the primary winding terminals of the transformer for the specified duration. More particularly, the high voltage pulse involves generating the voltage as discussed above, while concurrently triggering the switch 226 to permit the energy reservoir 221 to discharge through the primary winding 224. As the voltage of the reservoir 221 is multiplied by the transformer 224, a high voltage is created at the electrodes 230–231. This voltage is the additive sum of the voltages stored in the energy reservoirs 220–221. Alternatively, a lesser "high" voltage output may be created solely by triggering the switch 226, without involving the switch 227.

One or more of the above-mentioned pulses are therefore generated in task 404 to produce the user-specified pulse pattern. After the user-specified pulsing pattern is created completed in task 404, the routine 400 ends in task 406.

Operation With Preferred Pulsing Pattern

As mentioned above, the pulse generator 200 provides a user-specified pulse pattern comprising one or more pulses of "high" and/or "low" output voltage. FIGS. 5–9 illustrate various exemplary pulse shapes, which may be used alone or in combination to constitute the user-specified pulsing scheme.

Although each of the pulsing patterns of FIGS. 5–9 may provide distinct advantages for different applications, the following description highlights the features and operation of a pattern 700 (FIG. 7) to illustrate the operation of the invention, both electrically in the pulse generator 200 as well as physiologically in a cell sample.

The pattern 700 comprises a "stepped pattern", in that it provides first, second, and third voltage levels 702–704. One, two, or all of these voltages may be the same, if desired. The pulses have first, second, and third durations 706–708. In the present example, the first and third voltages 706, 708 provide a 500 V (D.C.), whereas the second voltage 707 provides 3000 V (D.C.).

Figure 10:
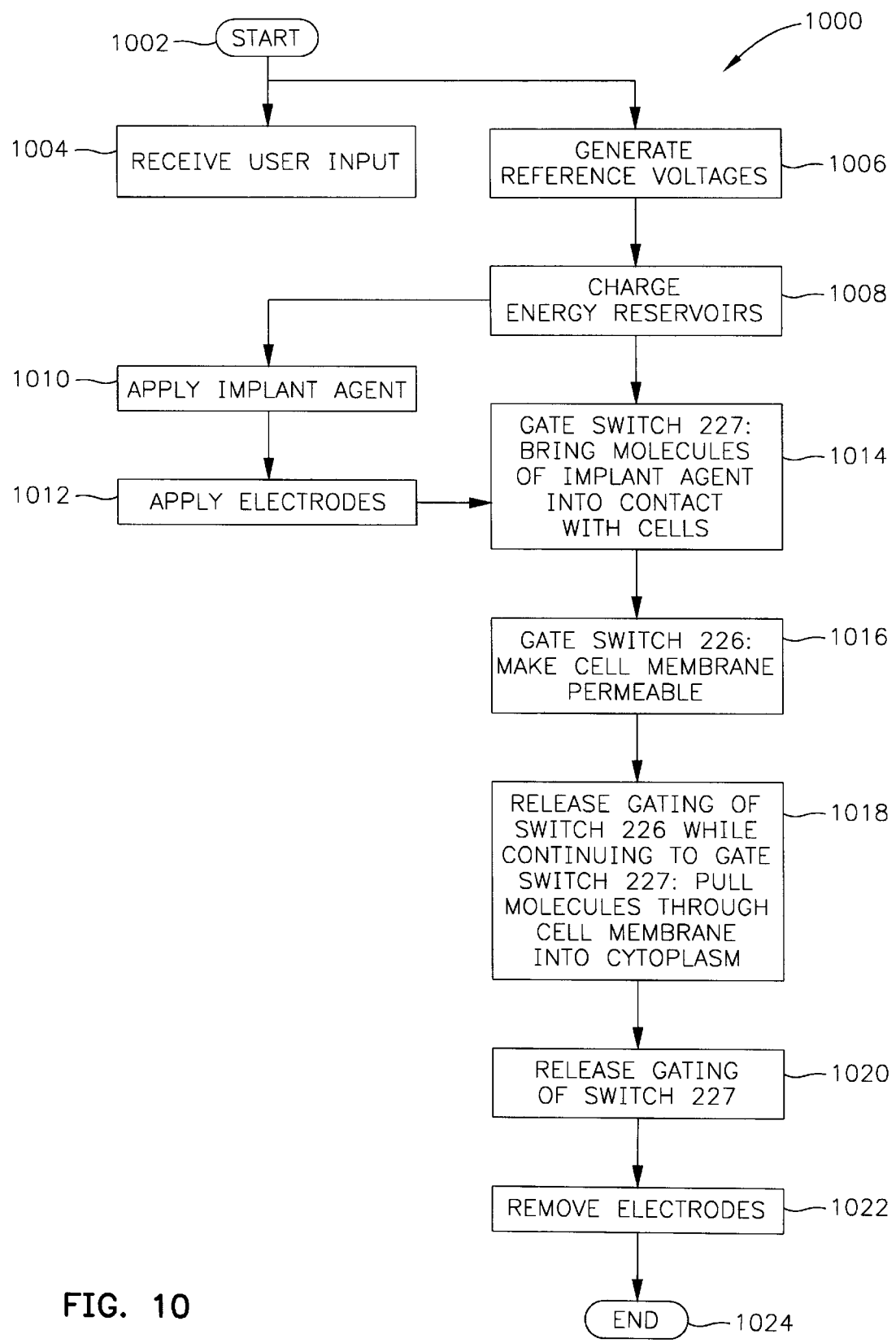
FIG. 10 is a flowchart illustrating an exemplary sequence of method steps in accordance with one example of the present invention.

FIG. 10 describes an illustrative sequence 100 involved in generating and applying the stepped pattern 700, and the physiological effects caused by application of the pattern 700. After the sequence begins in task 1002, the user interface 242 receives user input in task 1004. In the illustrative embodiment, the user input includes the user's specification of a desired electroporation pulsing pattern, including a duration and voltage level for each portion of the pattern.

In an alternative embodiment, the user may specify a desired magnitude of electric field to be applied by the transformer 224, and a measurement of the gap between the electrodes 230–231. In this case, the controller 240 may compute the appropriate voltage for the transformer 224 to generate in order to apply the desired electric field, for example by multiplying the electric field by the gap. In one embodiment, the gap measured may be input by the user manually. Alternatively, the gap may be mechanically measured and electronically fed to the controller 240 by automated means such as shown in U.S. Pat. No. 5,439,440, which is hereby incorporated by reference in its entirety.

Concurrently with task 1004, the power supply 202 generates the reference voltages at the output nodes 208–209. In the present example, the reference voltages 208–209 of 500 V (D.C.) are used. Generation of the reference voltages in task 1008 charges the energy reservoirs in task 1008.

After the task 1008, an operator in task 1010 applies molecules of an implant agent to a treatment site. The implant agent may comprise one or more types of DNA, genes, and/or various chemical agents. In the case of electrochemotherapy, one beneficial implant agent is Bleomycin.

With a live patient, the treatment site comprises a region of live cells, and the operator is preferably a nurse or physician who applies a liquid implant agent by injecting it with a hypodermic needle.

In the case of in vitro application of the implant agent, however, the treatment site may constitute a cell sample placed in an appropriate container. In this example, the operation may be a laboratory technician that applies a liquid implant agent by pouring, eye-dropping, or otherwise introducing the agent into the cell sample.

Step 1010, whether performed in vivo or in vitro, places the implant agent between the interstices of the cells at the treatment site. Next, in task 1012 the operator applies electrodes to the treatment site. In the case of a live patient, this may involve gripping a region of cells through the dermic with a caliper, inserting a needle array into the patient's tissue, or another procedure. With an in vitro treatment site, task 1012 may involve placing the cell sample between a pair of plate-shaped electrodes provided for that purposes. As an example, plate-shaped electrodes may be used, such as the BTX brand cuvettes, part number 640.

After task 1012, the controller 240 in task 1014 gates the switch 227, discharging the energy reservoir 220 and thereby applying the "low" voltage to the electrodes 230–231. This step accumulates molecules of the implant agent near the membranes of the cells in the cell sample. As discovered by the present invention, this step may be adequately performed with a reduced voltage. Accordingly, the "low" voltage of the energy reservoir 220 achieves with purpose, while still avoiding damage to the cells in the sample and saving electrical energy.

Figure 7:
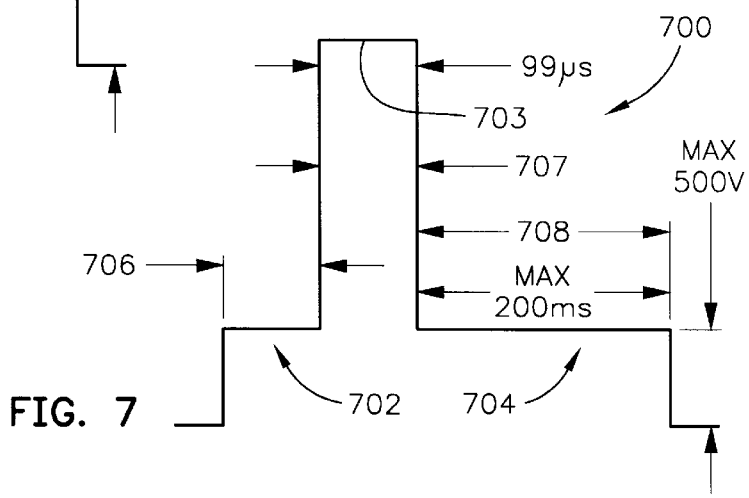
Figure 8:
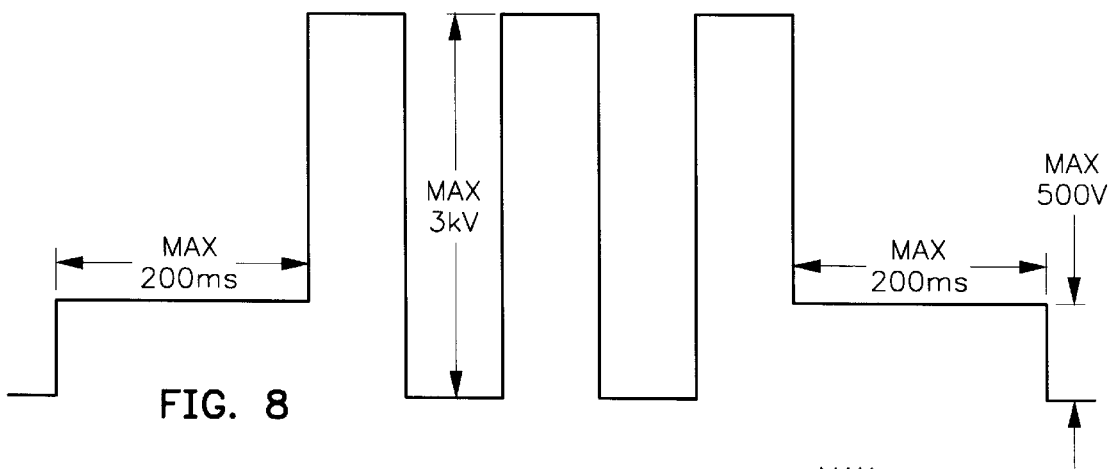
Figure 9:
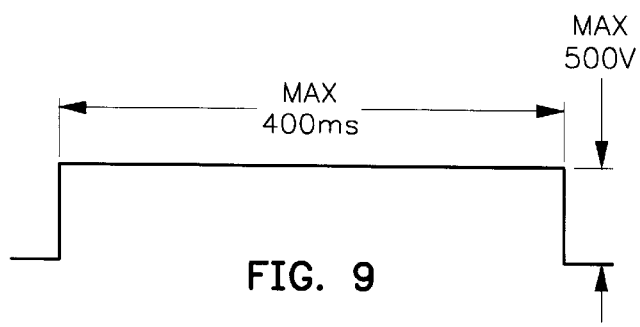

FIG. 7 illustrates task 1014 as the voltage pulse 702. As shown, this pulse preferably comprises a square wave having a duration 706 of about 10–200 msec and a voltage of about 500 V (D.C.). Depending upon the application, however, different parameters may be substituted to define the pulse 702.

After task 1014, the controller 240 in task 1016 gates the switch 226 (while continuing to gate the switch 227). This creates a "voltage" voltage upon the electrodes 230–231, corresponding to the sum of the reference voltages 208–209. This high voltage is sufficient to safely create small pores in the cells of the tissue sample. This inventors believe this effect to result from electrophoresis, the action of Coloumb forces on the charged molecules of the implant agent.

FIG. 7 illustrates this step as the voltage pulse 703. As illustrated, this pulse preferably comprises a square wave having a duration 707 of about 100 μsec and an electric field magnitude of about 1200 V/cm. Depending upon the application, however, different parameters may be substituted to define the pulse 702.

Advantageously, the pulse generator 200 automatically limits damage to cells of the tissue sample during this step. In particular, when the voltage from the primary winding 224a saturates the secondary winding 224b, the voltage presented by the secondary winding 224b begins to decay, in accordance with known principles of transformer operation. Thus, even if the voltage applied to the primary winding 224a is applied for an excessive length of time, the secondary winding 224b automatically limits the tissue sample's exposure to this high voltage pulse.

Next, in task 1018 the controller 240 ceases gating of the switch 226 while continuing to gate the switch 227. This step permits the molecules of the implant agent to transit the cells' permeable membranes, and enter the cells' cytoplasm.

FIG. 7 illustrate this step as the voltage pulse 704. As illustrated, this pulse preferably comprises a square wave having a duration 708 of about 1–200 msec and a voltage of about 500 V (D.C.). Depending upon the application, however, different parameters may be substituted to define the pulse 704.

After task 1018, the controller 240 releases gating of the switch 227, ending the pulse 700. Then, the operator removes the electrodes from the cell sample in task 1022, and the sequence 1000 ends in task 1022.

OTHER EMBODIMENTS

While there have been shown what are presently considered to be preferred embodiments of the invention, it will be apparent to those skilled in the art that various changes and modifications can be made herein without departing from the scope of the invention as defined by the appended claims.

What is claimed is:

1. An electroporation method, comprising the steps of:
   (a) applying an electric field of a first predetermined magnitude to a region of cells for a first predetermined duration;
   (b) increasing the electric field to a second predetermined magnitude greater than the first predetermined magnitude; and
   (c) reducing the electric field to a third predetermined magnitude less than the second predetermined magnitude,
   wherein the second predetermined magnitude is not substantially equal to the first or the third predetermined magnitudes.

2. An electroporation method, comprising the steps of:
   (a) positioning a pair of electrodes relative to a region of cells and delivering a predetermined implant agent to the region of cells;
   (b) moving molecules of the implant agent toward the cells by applying a voltage of a first predetermined magnitude to the electrodes for a first predetermined time;
   (c) creating pores in a plurality of the cells by applying a voltage of a second predetermined magnitude greater than the first predetermined magnitude to the electrodes for a second predetermined time; and
   (d) moving molecules of the implant agent into a plurality of the pores by applying a voltage of a third predetermined magnitude less than the second predetermined magnitude,
   wherein the second predetermined magnitude is not substantially equal to the first or the third predetermined magnitudes.

3. The method of claim 2, the second predetermined magnitude of voltage providing a resultant electric field at the electrodes in the range of 300–3000 V/cm.

4. The method of claim 3, further comprising the steps of computing the second predetermined magnitude of voltage by multiplying a desired electric field by measurement of a gap existing between the electrodes.

5. The method of claim 2, the first and third predetermined magnitudes of voltage being minimized to minimize damage to the cells due to thermal heating.

6. A method for generating an electroporation pulse pattern using an electroporation pulse apparatus that includes a transformer including a primary winding and a secondary winding, said method comprising the steps of:
   receiving user input specifying an output pulse pattern of one or more output pulses, said user input specifying a duration for each pulse and also specifying either a first predetermined output level or a second predetermined output level;
   for each pulse of the second predetermined output level, applying a first predetermined voltage to the secondary winding terminals of the transformer for the specified duration; and
   for each pulse of the second predetermined output level, applying the first predetermined voltage to the secondary winding terminals of the transformer while concurrently applying a second predetermined voltage, not substantially equal to the first predetermined voltage, to the primary winding terminals of the transformer for the specified duration.

7. The method of claim 6, further comprising the steps of:
   before the applying steps, arranging electrodes about a treatment site, said electrodes being coupled across the secondary winding terminals;
   before the applying steps, delivering molecules of a predetermined implant agent to the treatment site; and
   after the applying steps, removing the electrodes from the treatment site.

8. The method of claim 6, the treatment site comprising a region of tissue within a living being.

9. The method of claim 6, the treatment site comprising cells removed from a living being.

10. The method of claim 6, the user input further including at least one of the first and second predetermined voltages.

11. A method for generating a stepped electroporation pulse pattern at secondary winding terminals of a transformer, said transformer also including a primary winding electromagnetically coupled to the secondary winding and having a pair of primary winding terminals, said method comprising the steps of:
    (a) generating a first voltage at the secondary winding terminals by applying a first voltage to the secondary winding terminals;
    (b) a predetermined delay after initiating step (a), maintaining application of the first voltage at the secondary winding terminals while concurrently applying a second voltage, not substantially equal to the first voltage, to the primary winding terminals; and
    (c) a predetermined delay after initiating step (b), ceasing application of the second voltage to the primary winding terminals and maintaining application of the first voltage at the secondary winding terminals for a predetermined duration.

12. The method of claim 11, further comprising the steps of after step (c), ceasing application of the first and second voltages to the transformer.

13. The method of claim 11, further comprising the steps of:
    before step (a), arranging electrodes about a region of living cells said electrodes being coupled to the secondary winding terminals;
    before step (a), delivering molecules of a predetermined implant agent to the region; and
    after step (c), removing the electrodes from the region.

14. The method of claim 13, the region comprising tissue within a living being.

15. The method of claim 13, the region comprising cells removed from a living being.

16. An article of manufacture comprising a data storage medium tangibly embodying a program of machine-readable instructions executable by a digital processing apparatus to perform method steps for generating an electroporation pulse pattern in an electroporation pulse apparatus that includes a transformer including a primary winding, said method steps comprising:
    receiving user input specifying an output pulse pattern of one or more output pulses, said user input specifying a duration for each pulse and also specifying either a first predetermined output level or a second predetermined output level;
    for each pulse of the second predetermined output level, applying a first predetermined voltage to the secondary winding terminals of the transformer for the specified duration; and
    for each pulse of the second predetermined output level, applying the first predetermined voltage to the secondary winding terminals of the transformer while concurrently applying a second predetermined voltage, not substantially equal to the first predetermined voltage, to the primary winding terminals of the transformer for the specific duration.

17. An article of manufacture comprising a data storage medium tangibly embodying a program of machine-readable instructions executable by a digital processing apparatus to perform method steps for generating a stepped electroporation pulse pattern at secondary winding terminals of a transformer, said transformer also including a primary winding electromagnetically coupled to the secondary winding and having a pair of primary winding terminals, said method steps comprising the steps of:

(a) generating a first voltage at the secondary winding terminals by applying a first voltage to the secondary winding terminals;

(b) a predetermined delay after initiating step (a), maintaining application of the first voltage at the secondary winding terminals while concurrently applying a second voltage, not substantially equal to the first voltage, to the primary winding terminals; and (c) a predetermined delay after initiating step (b), ceasing application of the second voltage to the primary winding terminals and maintaining application of the first voltage at the secondary winding terminals for a predetermined duration.

18. An article of manufacture comprising a data storage medium tangibly embodying a program of machine-readable instructions executable by a digital processing apparatus to perform method steps for electroporation, said method steps comprising:

(a) applying an electric field of a first predetermined magnitude to a region of cells for a first predetermined duration;

(b) increasing the electric field to a second predetermined magnitude greater than the first predetermined magnitude; and (c) reducing the electric field to a third predetermined magnitude less than the second predetermined magnitude, wherein the second predetermined magnitude is not substantially equal to the first or the third predetermined magnitudes.

* * * * *